United States Patent [19]

Perlin

[11] 4,324,248
[45] Apr. 13, 1982

[54] MICROSURGICAL CLIP

[75] Inventor: Alfred R. Perlin, Highland Park, Ill.

[73] Assignee: Metatech Corporation, Northbrook, Ill.

[21] Appl. No.: 154,613

[22] Filed: May 30, 1980

[51] Int. Cl.³ ............................................. A61B 17/12
[52] U.S. Cl. .................................... 128/325; 128/346; 24/252 R
[58] Field of Search ............... 128/325, 326, 346, 321, 128/354; 251/9, 10; 24/255 R, 248 R, 252 R; D24/27; 81/43

[56] References Cited

U.S. PATENT DOCUMENTS

| 3,106,214 | 10/1963 | Reiner | 24/252 R X |
| 3,509,882 | 5/1970 | Blake | 128/325 |
| 3,766,925 | 10/1973 | Rubricius | 128/346 |
| 3,911,926 | 10/1975 | Peters | 128/325 |

FOREIGN PATENT DOCUMENTS 430945  8/1967  Switzerland ........................ 128/346

OTHER PUBLICATIONS

Automobile Trade Journal pp. 112 and 332 Jul. 1913.

Primary Examiner—Michael H. Thaler
Attorney, Agent, or Firm—Leydig, Voit, Osann, Mayer & Holt, Ltd.

[57] ABSTRACT

A microsurgical clip for clamping of small blood vessels formed of a hollow shell having openings top and bottom with an integral duck bill extending forwardly from the lower edge of its front wall. A cooperating insert of inverted "U" shape is nested in the housing to define a central pocket and terminates in a duck bill which cooperates with the duck bill of the shell. The shell and the insert have their back walls hinged together, and an expansible spring is seated in the pocket with one end coupled to the shell and the other end coupled to the insert for urging the insert upwardly into the shell to bias the duck bills together. The insert has a crown which projects upwardly through the opening at the top of the shell so that upon application of pinching pressure the insert is pressed downwardly with respect to the shell to compress the spring and to spread the duck bills for clamping engagement of a blood vessel therebetween. In one embodiment of the invention the spring is retained in the pocket by a trap door which encloses the bottom of the shell. The shell, insert and trap door are preferably molded of plastic integrally with one another.

12 Claims, 11 Drawing Figures

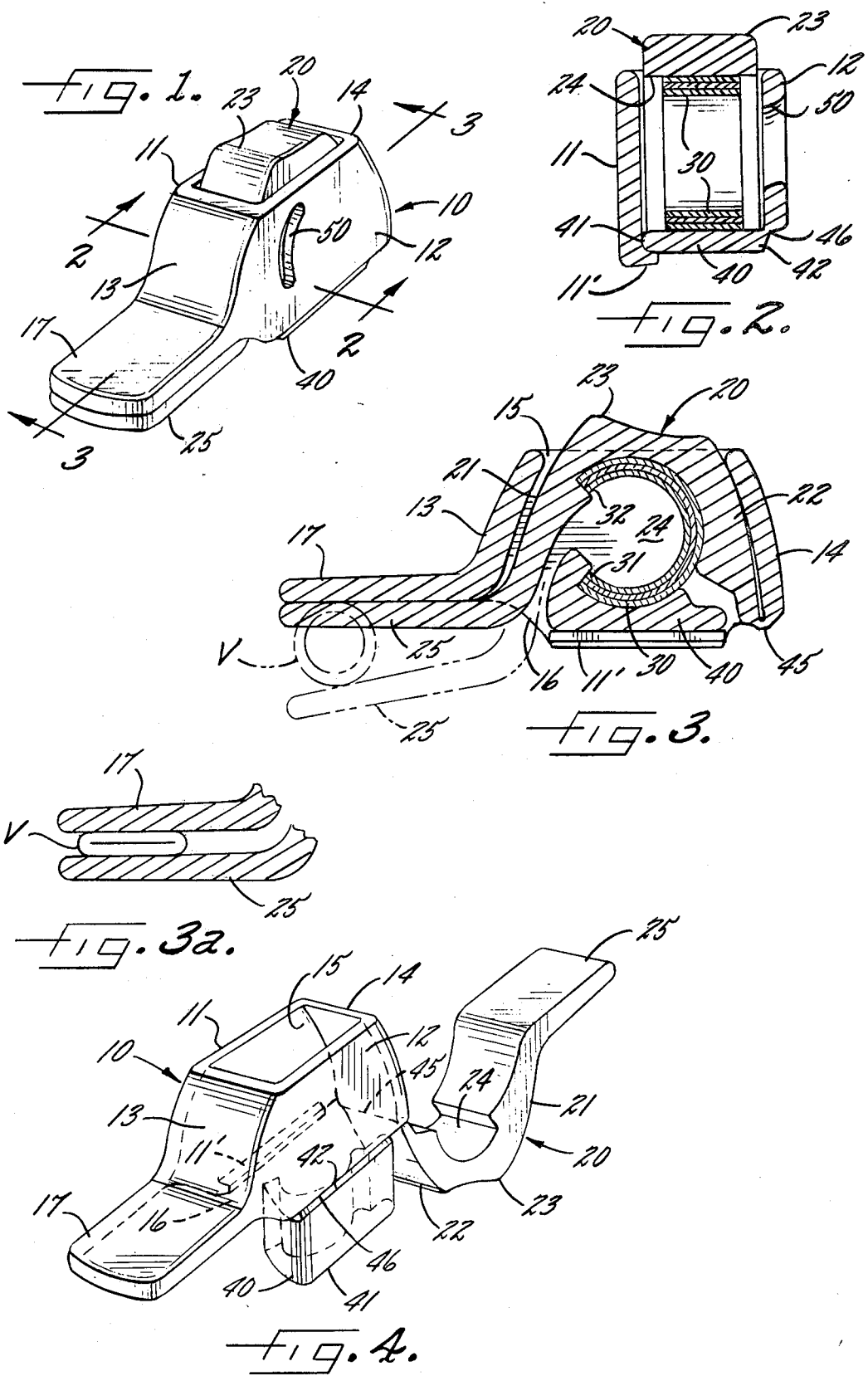

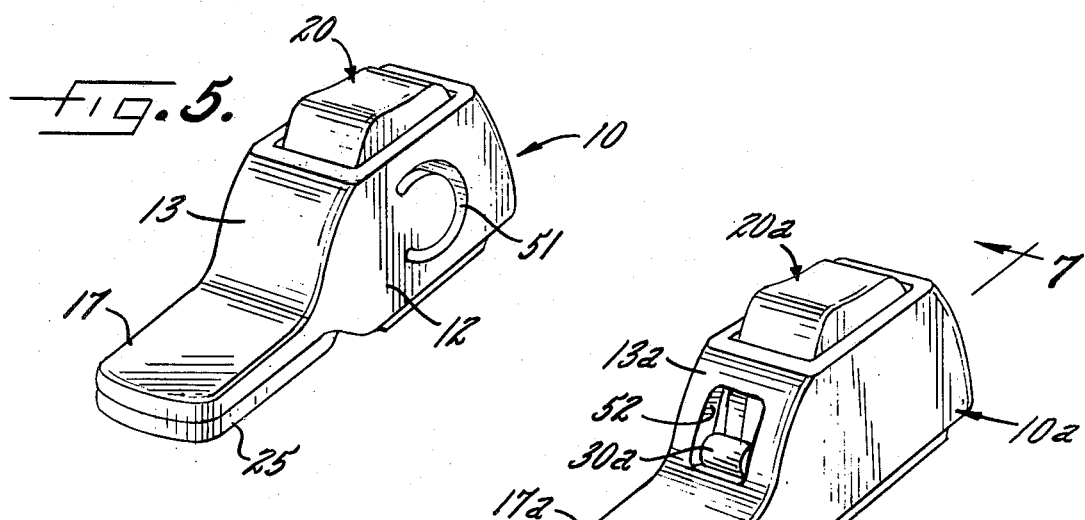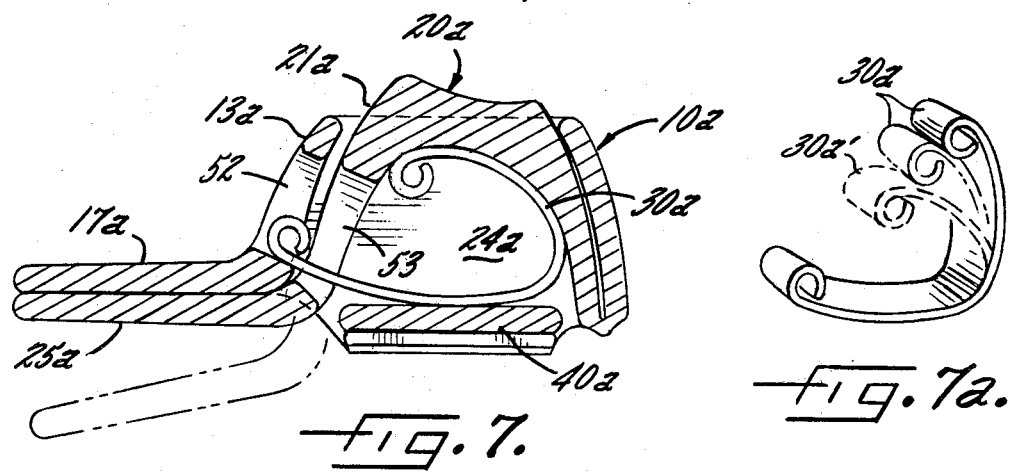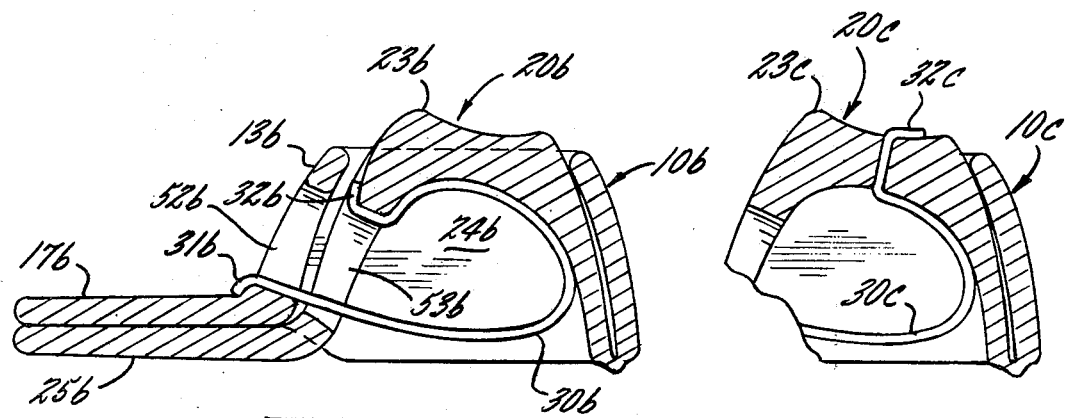

MICROSURGICAL CLIP

In doing surgery on parts of the body which are supplied by numerous small blood vessels it is necessary to clamp off the blood vessels individually in order to reduce the amount of blood discharged into the field. The clamps which have been available for this purpose in the past have been of unwieldy construction applying pressure which is highly localized, usually excessive, and largely unpredictable so that blood vessels are often crushed or otherwise irreparably damaged. Nevertheless such clamps, particularly those intended for specialized purposes such as brain surgery, have been extremely expensive. Finally, prior surgical clamps have commonly been of multi-piece construction running the risk that a piece of the clamp may be left in the wound.

It is accordingly an object of the present invention to provide a microsurgical clip for clamping of small blood vessels which will not crush or otherwise injure even the most fragile of vessels. It is a related object to provide a microsurgical clip in which the clamping force may be precisely determined by pre-calibration of the metal spring which exerts the clamping force.

It is a more specific object in this connection to provide a microsurgical clip which is of uniform construction but which may be fitted with springs in increments of stiffness and identified, if desired, by color coding, so that the clamping force may be tailored to the type and size of blood vessel being clamped.

It is a further object of the invention to provide a microsurgical clip which consists of a single plastic piece plus a spring secured intimately together so that there is no possibility of losing a part of the clip in the wound. Thus it is an object to provide a clip which can be used with confidence by a surgeon and which, in addition, is easily grasped and operated with light pinching pressure, and with no risk of overstressing the spring.

It is one of the important objects of the present invention to provide a microsurgical clip which is highly economical, which can be molded of plastic in one piece and in which the spring which provides the clamping force may be quickly and easily inserted into secure operating position. Because of its economy the clip may be discarded after use or, if desired, readily sterilized for re-use.

Other objects and advantages of the invention will become apparent upon reading the attached detailed description in reference to the drawings in which:

FIG. 1 is a perspective view showing a microsurgical clip constructed in accordance with the invention.

FIG. 2 is a transverse section taken along line 2—2 in FIG. 1.

FIG. 3 is a longitudinal section taken along line 3—3 in FIG. 1.

FIG. 3a is a fragmentary side view showing the clamping of a blood vessel.

FIG. 4 is a perspective view showing the plastic portion of the device with the elements integrally molded in swung-apart relation.

FIG. 5 is a perspective view similar to FIG. 1 but showing a modified opening in the shell for insertion of the clamping spring.

FIG. 6 is a perspective view similar to FIG. 5 but showing a different spring insertion opening.

FIG. 7 is a longitudinal section looking along line 7—7 in FIG. 6.

FIG. 7a is a fragmentary perspective of one form of spring usable in the embodiment of FIGS. 6 and 7.

FIG. 8 shows a variation of the construction of FIG. 7 permitting omission of the trap door element.

FIG. 8a is a fragment showing an alternative anchoring means for the spring of FIG. 8.

While the invention has been described in connection with several preferred embodiments, it will be understood that I do not intend to be limited to the particular embodiments shown but intend, on the contrary, to cover the various alternative and equivalent constructions included within the spirit and scope of the appended claims.

Turning now to FIGS. 1-3 there is shown a microsurgical clip constructed in accordance with the invention formed of a hollow shell or housing 10 in the form of a box having generally trapezoidal side walls 11, 12 and opposed front and back walls 13, 14 defining extensive top and bottom openings 15, 16 (see also FIG. 4). Extending forwardly from the lower edge of the front wall 13, and coextensive in width, is a flat integral duck bill 17. By "duck bill" is meant a clamping element presenting an extensive flat surface, free of teeth, which mates with a similar clamping element.

Nested in the shell is a cooperating insert 20 of inverted "U" shape, the insert having a front wall 21 and back wall 22 and crown 23 defining a central pocket 24. The front wall of the insert terminates in a forwardly extending integral duck bill 25 which cooperates, coextensively as shown in the drawings, with the duck bill 17 of the shell.

In carrying out the invention an expansible spring is seated in the pocket of the insert, having one end coupled to the shell and the other end coupled to the insert for urging the insert relatively upwardly into the shell thereby biasing the duck bills into resilient clamping engagement with one another. The spring, indicated at 30, is of "C" shape having a first end 31 and a second end 32, with the open side facing in the direction of the duck bills. The spring may be formed of a single leaf, or layer, of resilient metal, outwardly sprung, or may be formed of a plurality of leaves, or laminations, telescoped together depending upon the clamping force which is desired.

For the purpose of keeping the spring seated in the pocket 24 the shell preferably has a trap door 40 enclosing its bottom opening 16. The trap door in the present instance consists of a rectangular flap having lateral edges 41, 42 which extend along the side walls 11, 12 of the shell. The edge 41 of the trap door may be captured by a lip, or ledge, 11' at the lower edge of the side wall 11 of the shell.

In accordance with one of the features of the invention the shell, insert and trap door are all formed of resilient durable plastic having respective strips of greatly reduced cross section between them forming integral "live" hinges whereby the clip may be molded in swung-apart condition as a single piece of plastic, the portions of which may then be swung together to form a working assembly. The live hinge between the shell and insert is indicated at 45 in FIG. 3 and the live hinge between the shell and trap door is indicated at 46 in FIG. 2. The cross section of the hinge 45 is purposely made extremely thin so that it bends easily and does not exert any appreciable amount of torque between the connected elements with the result that the clamping force exerted at the bills is precisely predeterminable, depending only upon the strength of the calibrated spring which is used.

To make the insert accessible for application of pinching pressure, the top, or crown, 23 of the insert is dimensioned to extend through the opening 15 at the top of the shell. Thus pinching pressure applied between the finger tips against the crown of the insert and the trap door of the shell, respectively, opens the clip to engage a vessel V, with subsequent release gently flattening the vessel as shown in FIG. 3a.

The device is readily assembled by swinging the insert 20 inwardly and upwardly into nested position, followed by insertion of the spring 30 and closing of the trap door 40, with the free edge of the trap door being snapped behind the ledge 11' on the side wall 11.

However, in carrying out the invention in one of its aspects an opening is provided in the shell so that the spring may be inserted into the central pocket 24 after the trap door has been closed. Thus I provide an arcuate opening 50 in the side wall 12 of the shell. Such opening may, in the form of the invention illustrated in FIG. 1, be relatively short and angled so as to permit feeding of the spring 30 into the pocket, or the individual laminations thereof, longitudinally but angled in a direction such that the spring assumes a seated "C" configuration upon being fully inserted.

Alternatively, the insertion opening formed in the side wall 12 of the shell may itself be "C" shaped as shown at 51 in FIG. 5 for broadwise insertion of the spring. The dimension of the "C" is preferably less than the dimension of the pocket 24 which receives the spring so that the spring is inserted in a compressed state, expanding outwardly into seated position within the pocket as soon as it clears the insertion opening.

One advantage of the use of an insertion opening for the spring is that springs of different force calibration can be inserted into seated position depending upon the clamping force desired and even though the trap door is sealed shut.

In accordance with one of the aspects of the present invention the shell and insert may be provided with registering openings in their front walls for insertion of the spring into seated position. Such construction is shown in FIG. 7 where corresponding reference numerals are employed to indicate parts of the device common to the preceding embodiment but with addition of subscript a. Thus the front wall 13a of the shell has formed therein an opening 52 while the front wall 21a of the insert has a registered opening 53. Such openings permit the C-shaped spring 30a to be compressed and slipped into its illustrated seated position in which the upper loop of the spring presses upwardly against the insert and the lower loop presses downwardly against the trap door. The spring may be in the form of a leaf having three conditions illustrated in FIG. 7a. The first or unstressed state is indicated by the full lines, while the dot-dash lines indicate the pocketed and fully compressed conditions, respectively.

If desired the spring 30a, instead of being formed as a leaf spring, may be formed as a loop of spring wire having the profile set forth in FIG. 7a.

It may be noted that the trap door 40 may be omitted without departing from the invention in its broader aspects. This is shown, by way of example, in FIG. 8 where corresponding elements have been indicated by corresponding reference numerals with addition of subscript b. Here the shell 10b and insert 20b are formed with registering openings 52b, 53b, respectively. The C-shaped spring 30b is formed so that its lower end 31b extends through clearance opening 53b to engage the lower edge of the opening 52b in the shell. The upper end 32b of the spring similarly engages the upper edge of the clearance opening 53b in the insert. With the spring 30b pre-sprung in the expanding direction, the effect of the spring is to urge the insert into its nested condition, thereby applying resilient force between the duck bills 17b, 25b. In assembling the device the spring 30b may be inserted either through the hollow bottom or through the registering openings 52b, 53b. The lack of a bottom, or trap door, surface does not affect usage of the device since it is constructed on such a small scale that the tip of the surgeon's finger readily bridges the distance between the side walls of the shell in applying pinching pressure to the crown 23b of the insert.

While the spring 30b, seated as shown in FIG. 8, is adequately secure, additional security may, if desired, be provided by anchoring the upper end of the spring captively with respect to the insert as shown in FIG. 8a. It will be noted that the upper end of the spring, indicated at 32c, extends through a clearance opening in the crown 23c of the insert with its tip bent over to insure retention.

While the term "trap door" has been used to describe the integrally hinged rectangular flap 40 which encloses the bottom of the device I do not intend to limit the term to this particular form and it will be understood that the term is intended to cover any element which spans the central pocket to the extent that such element supports the spring in its position within the pocket. The term "trapezoidal" refers to a shell which is narrower at the top than at the bottom.

The disclosed form of clip has been found to be particularly advantageous in connection with brain surgery which requires the clamping of numerous small vessels varying in size and fragility and all of which are plentifully supplied with blood. The clip has, as a primary advantage, susceptibility to being made in extremely small sizes, for example, to a total length of, say, one centimeter. Because of the small size there is minimum clutter, even in a restricted field.

It is one of the features of the construction that the same size of clip may be used to apply different clamping pressures, as may be suited to blood vessels of different nature or of different size, by the simple expedient of using a spring, either single leaf or laminated, corresponding to the clamping force which is desired.

It has been the practice among certain surgeons in the past to calibrate each clamp just prior to usage in order to avoid clamps exerting excessive, and possibly damaging, force. Such "on site" calibration tends to interfere with the smooth flow of surgical procedure. Thus it is contemplated that the present design of clip may be calibrated and separated into categories, identified, if desired, by color coding, prior to surgical use. Indeed, it is one of the features of the construction that clamping force need not be measured in the unit itself; instead, only the spring need be calibrated, which can be accomplished in a simple force-measuring jig prior to insertion of the spring into place.

One advantage of using standard shell-insert units with a series of pre-calibrated springs to achieve different, but calibrated, amounts of clamping force is that the inventory of shell-inserts may be reduced to a minimum, resulting in still further economy.

It is, finally, one of the features of the present invention that the projection 23 of the insert 20 extends only a limited distance beyond the opening 15 at the top of the shell, a distance which is sufficient to enable the duck bill to grasp a blood vessel (FIG. 3) but a distance which is sufficiently small so that the spring 30 is not stressed beyond its elastic limit, even as the surgeon applies excessive pinching force. Thus, regardless of the amount of force applied, movement of the insert can only occur until the projection 23 is flush with the opening 15—beyond this point the finger tip of the surgeon bridges the opening. This inability to overstress the spring insures that the calibration of the spring is accurately maintained through repeated usages.

While a spring of "C" shape has been disclosed in connection with the above preferred embodiments of the invention, it will be understood by one skilled in the art that the invention is not necessarily limited to a spring of "C" configuration and that in the structure shown in FIGS. 1-3, for example, a helical spring may be used or, alternatively, a spring ribbon consisting of one or more spiraled convolutions. Friction between the convolutions may be overcome by an application of teflon, and such a spring may be inserted through the trap door 40 or fed endwise through the side opening 50, with the length of the ribbon being dependent upon the clamping force which is desired.

Also while the use of the live hinge, as shown at 45, is preferred where the device is molded of plastic, it will be apparent to one skilled in the art that the invention is not limited to a live hinge and that any conventional hinge construction may be substituted as desired, particularly where the clip is formed of metal rather than plastic.

What I claim is:

1. A microsurgical clip for clamping of small blood vessels comprising, in combination, a hollow shell in the form of a box having opposed side walls and opposed front and back walls but with openings extending over the top and bottom respectively, the shell having an integral duck bill extending forwardly at the lower edge of the front wall with the duck bill being substantially coextensive with the width of the front wall, a cooperating insert of inverted "U" shape conformingly nested in the shell, the insert having a front wall and a back wall respectively flatly adjacent the front and back walls of the shell, the insert having its back wall hinged edge-to-edge with the back wall of the shell, the front wall of the insert terminating in a forwardly extending duck bill which lies underneath and cooperates coextensively with the duck bill of the shell, the shell having a trap door enclosing its bottom opening so that a pocket is formed between the trap door and the insert, and an outwardly expansible spring interposed in the pocket between the trap door and the insert for urging the insert relatively upwardly into the shell thereby biasing the duck bills into resilient clamping engagement with one another, the insert having a projection which extends through the opening at the top of the shell so that upon application of pinching pressure to the projection the insert is pressed downwardly with respect to the shell compressing the spring accompanied by relative spreading of the duck bills for temporary unclamping of the duck bills and engagement of a blood vessel therebetween.

2. The combination as claimed in claim 1 in which the trap door is hinged along one of its side edges with means at the remote edge for captive engagement.

3. The combination as claimed in claim 2 in which the means providing captive engagement of the trap door is in the form of an integral internal ledge on the shell.

4. The combination as claimed in claim 1 in which the shell, insert and trap door are formed of resilient plastic having respective strips of reduced cross section between them forming integral live hinges whereby the clip may be molded as a single piece of plastic.

5. The combination as claimed in claim 1 in which a clearance opening is provided in the side wall of the shell for insertion of the spring.

6. The combination as claimed in claim 1 in which registering clearance openings are provided in the front walls of the shell and insert for insertion of the spring.

7. The combination as claimed in claim 6 in which the lower end of the spring bears against the lower edge of the opening formed in the front wall of the shell.

8. A microsurgical clip for clamping of small blood vessels comprising, in combination, a hollow shell in the form of a box having opposed side walls and opposed front and back walls but with openings extending over the top and bottom respectively, the shell having an integral duck bill extending forwardly at the lower edge of the front wall, with the duck bill being substantially coextensive with the width of the front wall, a cooperating insert of inverted "U" shape conformingly nested in the shell, the insert having a front wall and a back wall respectively flatly adjacent the front and back walls of the shell, the insert having its back wall hinged edge-to-edge with the back wall of the shell, the front wall of the insert terminating in a forwardly extending integral duck bill which lies underneath and cooperates coextensively with the duck bill of the shell, the insert having a clearance opening in its front wall, and a spring nested in the insert and extending through the clearance opening into engagement with the shell for urging the insert relatively upwardly into the shell thereby biasing the duck bills into resilient clamping engagement with one another, the insert having a projection which extends through the opening at the top of the shell so that upon application of pinching pressure to the projection the insert is pressed downwardly with respect to the shell compressing the spring accompanied by relatively spreading of the duck bills for temporary unclamping of the duck bills for engagement of a blood vessel therebetween.

9. A microsurgical clip for clamping of small blood vessels comprising, in combination, a hollow shell in the form of a box having opposed side walls and opposed front and back walls but with openings extending over the top and bottom respectively, the shell having an integral duck bill extending forwardly at the lower edge of the front wall, the shell having an integral duck bill extending forwardly at the lower edge of the front wall with the duck bill being substantially coextensive with the width of the front wall, a cooperating insert of inverted "U" shape conformingly nested in the shell and defining a central pocket, the insert having a front wall and a back wall respectively flatly adjacent the front and back walls of the shell, the insert having its back wall hinged edge-to-edge with the back wall of the shell, the front wall of the insert terminating in a forwardly extending integral duck bill which lies underneath and cooperates coextensively with the duck bill of the shell, and an expansible spring seated in the pocket having one end coupled to the shell and the other end coupled to the insert for urging the insert relatively upwardly into the shell thereby biasing the duck bills into resilient clamping engagement with one another, the insert having a projection which extends through the opening at the top of the shell so that upon application of pinching pressure to the projection the insert is pressed downwardly with respect to the shell compressing the spring accompanied by relative spreading of the duck bills for temporary unclamping of the duck bills and engagement of a blood vessel therebetween.

10. The combination as claimed in claim 1 or claim 8 or claim 9 in which the shell and insert are formed of resilient plastic having a strip of reduced cross section between them forming an integral live hinge.

11. The combination as claimed in claim 1 or in claim 8 or in claim 9 in which the distance that the projection extends upwardly of the opening at the top of the shell is limited to such an amount that when the projection is pressed to a position which is flush with the top of the shell the spring is stressed within its elastic limit.

12. The combination as claimed in claim 1 or in claim 8 or in claim 9 in which the side walls of the hollow shell have a generally trapezoidal profile.

* * * * *